US00PP33734P3

(12) United States Plant Patent
Maillard et al.

(10) Patent No.: US PP33,734 P3
(45) Date of Patent: Dec. 14, 2021

(54) APPLE TREE NAMED 'REGALNAT'

(50) Latin Name: *Malus domestica*
Varietal Denomination: REGALNAT

(71) Applicant: AGRO SELECTIONS FRUITS, Elne (FR)

(72) Inventors: Laurence Maillard, Elne (FR); Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/974,240

(22) Filed: Nov. 25, 2020

(65) Prior Publication Data

US 2021/0168980 P1 Jun. 3, 2021

(30) Foreign Application Priority Data

Nov. 29, 2019 (QZ) ..... PBR 2019/3252

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Birch, Stewart, Kolasch & Birch, LLP

(57) ABSTRACT

A new and distinct variety of apple tree denominated 'REGALNAT' produces high yield of firm fruits with large size, round slightly flattened shape, and a luminous dark red skin color, having exceptional eating quality; the fruit is further characterized by its good handling, its tolerance to main apple pests and diseases and its storage qualities.

5 Drawing Sheets

Latin name of the genus and species of the plant claimed: *Malus domestica* Borkh.

Variety denomination: 'REGALNAT'.

This application claims priority of Community plant variety right No. 2019/3252 filed on Nov. 29, 2019 (Nov. 29, 2019) which is hereby incorporated by reference in its entirety.

BACKGROUND OF THE NEW VARIETY

Field of the Invention

In the field of plant genetics, we conduct an extensive and continuing plant-breeding program including the organization and reproduction of orchard trees, among which apple, peaches, nectarines, apricots, and cherries are exemplary. It was against this background of our activities that the present variety of apple tree was originated and reproduced by us in our experimental orchard located near Elne, Pyrénées Orientales, France.

ORIGIN OF THE VARIETY

The present invention relates to a new a distinct variety of apple tree *Malus domestica* Borkh. which has been given the variety denomination 'REGALNAT'. This tree produces fruits with a long shelf life without alteration after harvesting, very good eating quality with a white flesh for fresh market in September or October in the Pyrénées Orientales department, France. Contrast is made to 'REGALYOU' apple tree variety (U.S. Plant Pat. No. 25,827) for reliable description. Contrast is also made to the parent varieties of 'REGALNAT', that are 'ARIANE 6407RT' (female or seed parent—non patented) and 'SELECTION INRA 6062RT' (male or pollen parent—non patented).

'REGALNAT' is a promising candidate for commercial success in that it produces very attractive fruits having a long shelf life.

The present new variety of apple tree (*Malus domestica* Borkh.) was developed by us in our experimental orchard located in France. 'REGALNAT' apple tree originated in a cultivated area of the South of France, in the Pyrénées-Orientales department where it was also tested. This zone also called Roussillon is subject to a Mediterranean climate. The winter is generally sweet and the summer is hot and dry. The total amount of cold hours lower than 7° C. (Celsius) varies from 700 hours to 1200 hours. The total amount of sunshine hours is an average of 2400 hours to 2800 hours per year. The prevailing wind is called "Tramontane": it dries the air and clear the sky from cloud, but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen, and the summer is dry with a few thunderstorms.

The 'REGALNAT' variety results from a pollinated cross between the 'ARIANE 6407 RT' apple tree (non patented) which was used as a seed parent and the 'SELECTION INRA 6062RT' apple tree (non patented) which was used as the pollen parent.

The 'REGALNAT' variety was obtained by hybridizing and propagated by grafting on a 'M9EMLA' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

SUMMARY OF THE NEW VARIETY

The new variety 'REGALNAT' produces fruits of large size, firm and crunchy, and with dark red color. The blooming period is medium for the variety, namely in the middle of April. The maturity period is considered late, usually at the end of September or early in October, in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
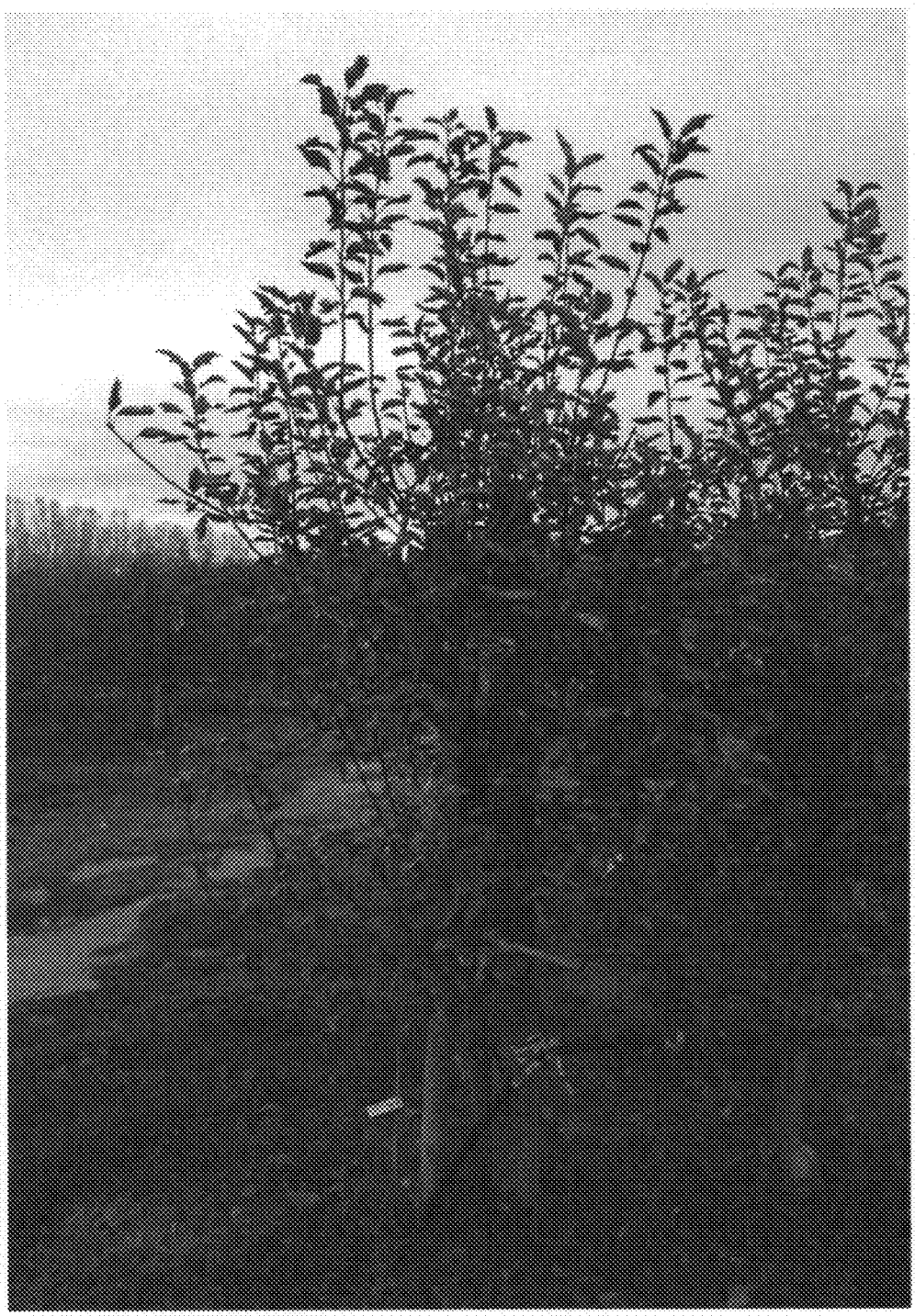
FIG. 1 is a color photograph which shows a tree of the new variety in orchard.
Figure 2:
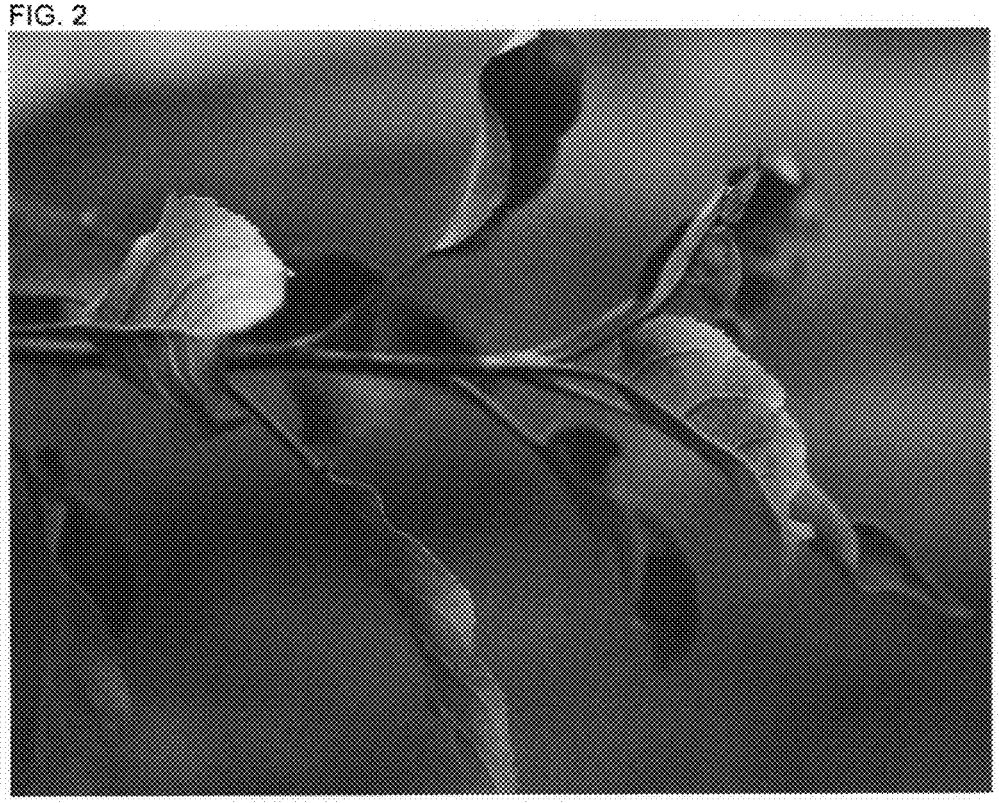
FIG. 2 is a close view of a branch of a tree of the new variety in orchard, for depicting the branches and leaves of the new variety.
Figure 3:
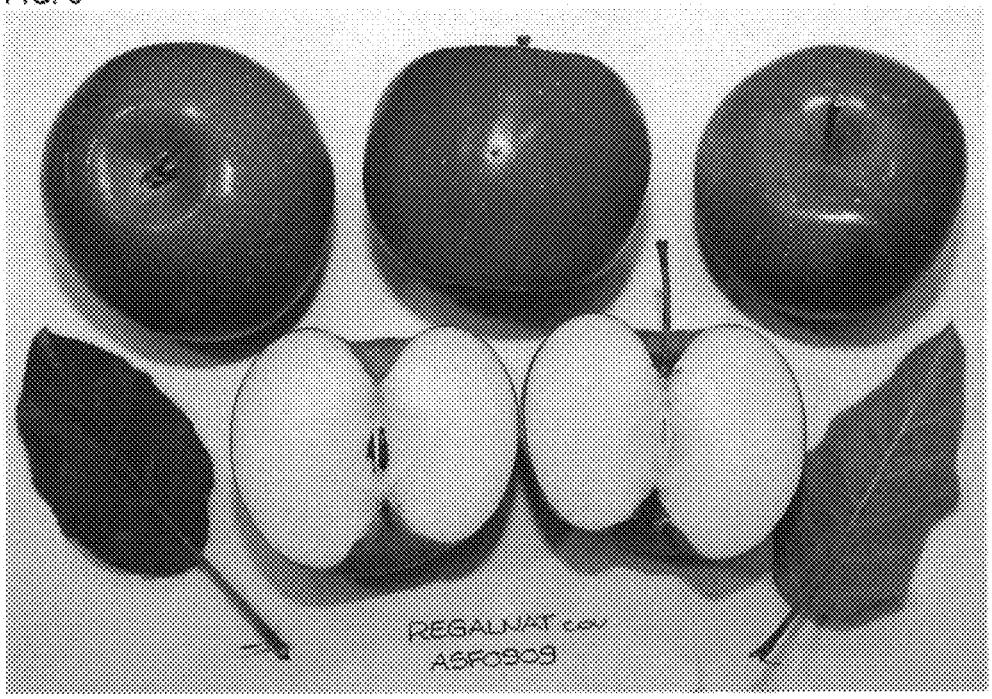
FIG. 3 is a color photograph which shows three whole fruits of the new variety at ripening time, and a fourth fruit, cut in a half in transverse cross section for depicting the fruit flesh, the seeds and the locules of the new variety; two leaves are also shown, for depicting both surfaces of the leaves.
Figure 4:
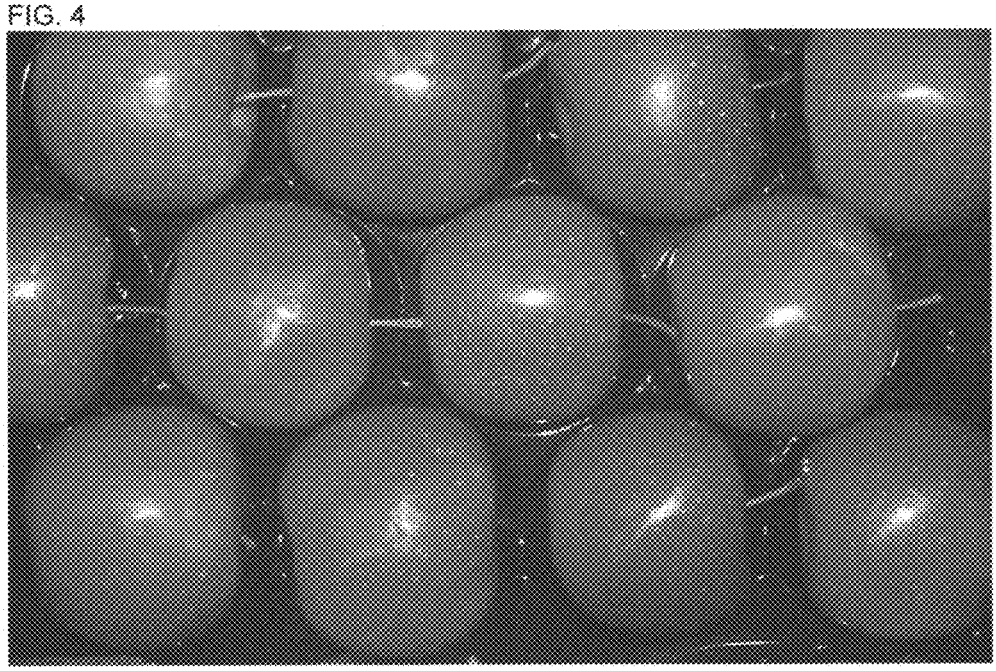
FIGS. 4 and 5 show close views of typical specimens of the new variety, at ripening time.
Figure 5:
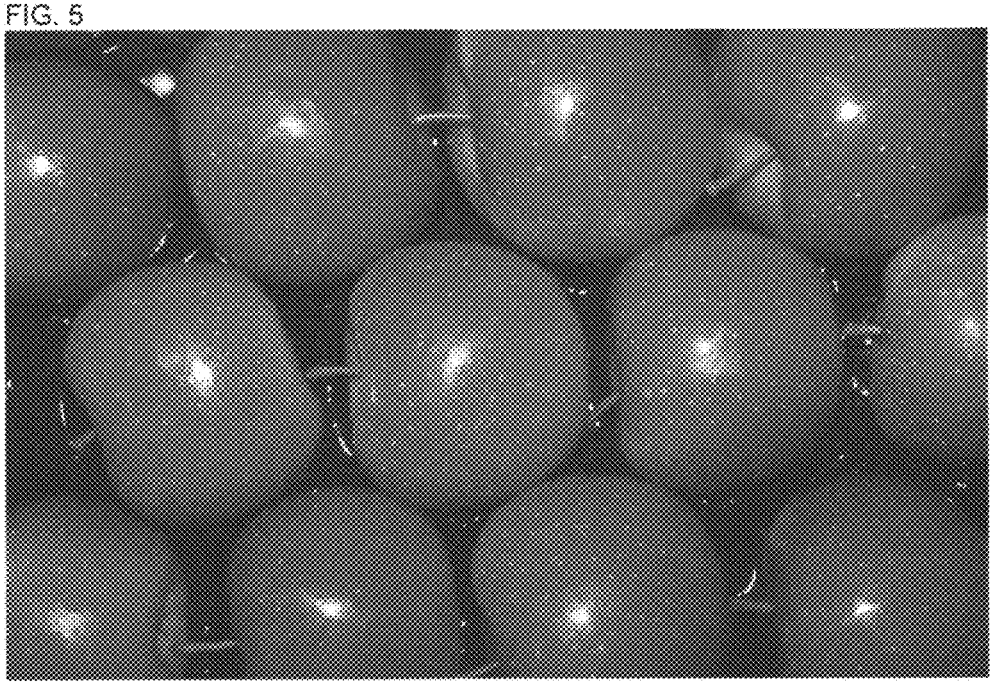
Figure 6:
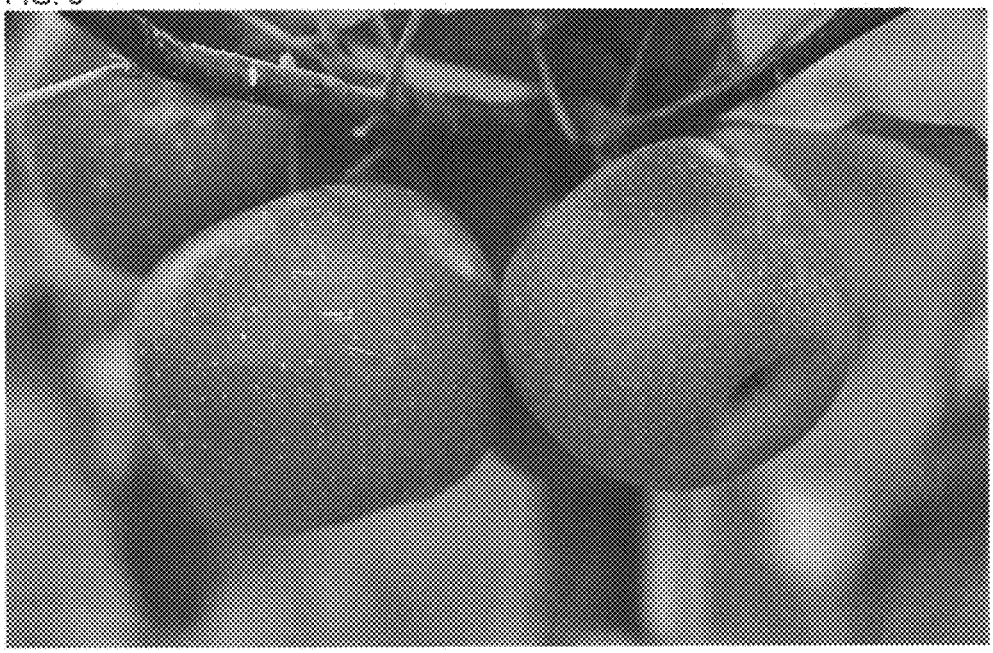
FIG. 6 is a close view of a branch of a tree of the new variety in orchard bearing fruits.
Figure 7:
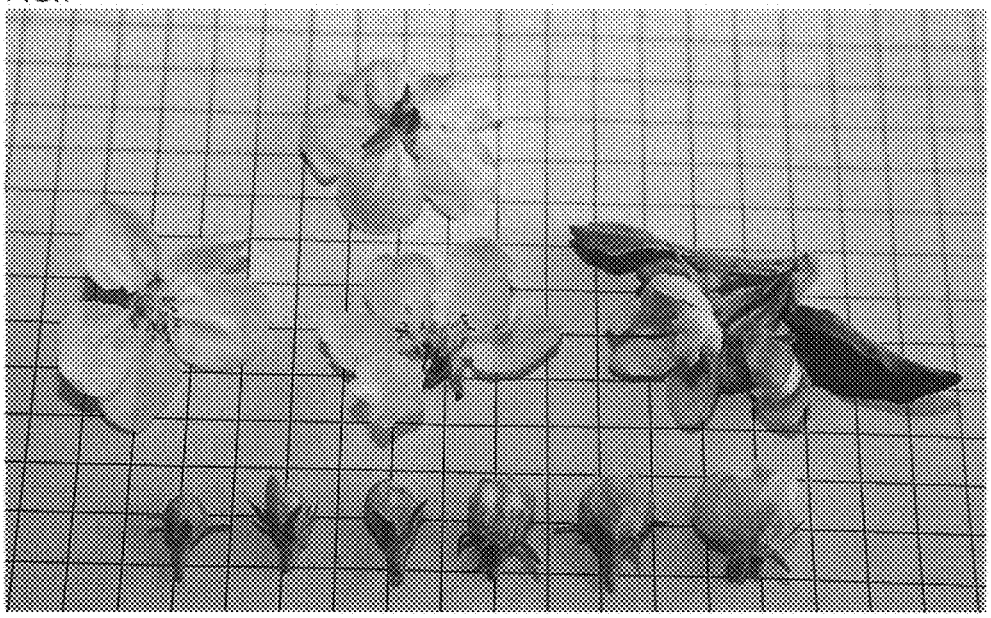
FIG. 7 shows typical flowers of 'REGALNAT' variety at blooming with some leaves for depicting the flower buds at different stages of development, the reverse and side view of the flowers and the reproductive organs of the new variety.
Figure 8:
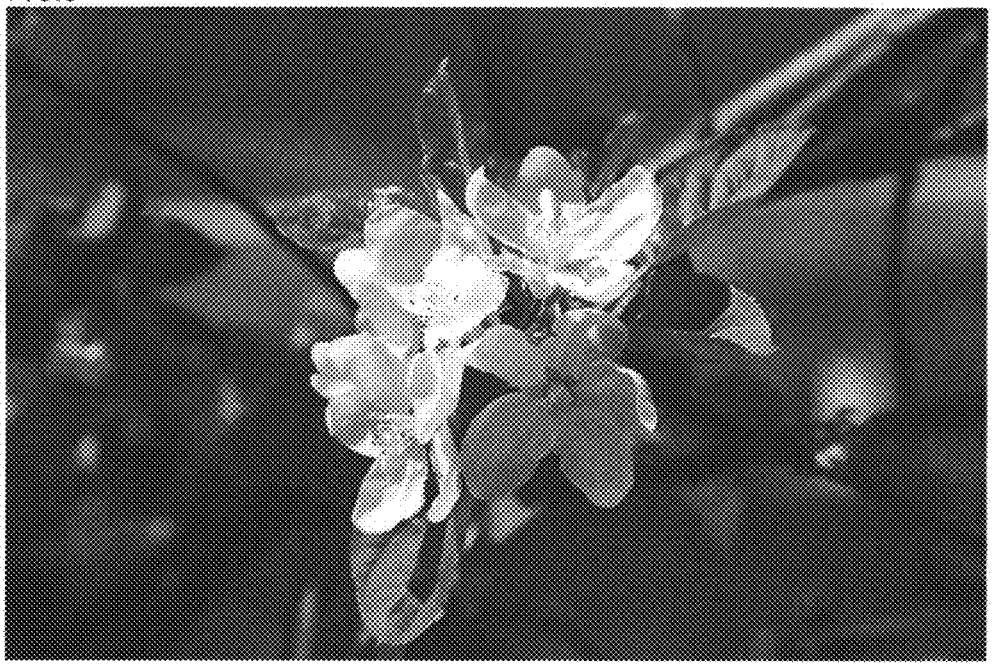
FIG. 8 shows a bunch of flowers of the new variety 'REGALNAT' at blooming time on tree, in orchard.

The enclosed photographs show plants in their fourth growing season (third year of production).

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of apple tree, its flowers, foliage and fruit, as based on observations of specimens grown near Elne, South of France, with color in accordance with The R.H.S. Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of semi-sweet apple are a large fruit size with a color of skin considered dark red. The fruit flesh is cream. The fruit is firm.

The time of beginning of flowering is medium whereas the time of beginning of fruit ripening is considered late.

In comparison with the 'REGALYOU' apple tree variety (U.S. Plant Pat. No. 25,827), 'REGALNAT' apple tree ripens earlier during the season. Namely, the fruits of 'REGALNAT' apple tree variety ripen 5 to 7 days before the fruits of 'REGALYOU' apple tree variety. Also, the blooming periods of 'REGALNAT' is also different from the blooming period of 'REGALYOU', as the flowers of 'REGALNAT' usually bloom a few days later than the flowers of 'REGALYOU'. Fruits are also different in regards of fruit shape: 'REGALNAT' fruits are considered to be round and very regular whereas the shape of 'REGALYOU' fruits is considered to be obloid, round to slightly flatten. The skin color of 'REGALYOU' fruits is considered bright red on approximately 70-80% of the fruit skin, whereas the fruit skin for 'REGALNAT' is colored with a very luminous red covering approximately 90 to 100% of the fruit skin surface, on a washed orange red background.

The flavor of the 'REGALNAT' fruit flesh is considered to be perfectly balanced between sugar and acidity, whereas the fruits of 'REGALYOU' present a lower acidity, with a semi-sweet taste.

Compared to its seed parent, which is the 'ARIANE 6407RT' apple variety (non patented), the fruits of the new variety 'REGALNAT' ripen approximately one week earlier. The fruits produced by the 'REGALNAT' variety are bigger than those produced by its seed parent (respectively between 75.0 and 80.0 millimeters, vs. between 65.0 and 75.0 millimeters). The skin color of 'ARIANE 6407RT' fruits is considered red on approximately 75% of the fruit skin, on a washed red background, whereas the fruit skin for 'REGALNAT' is colored with a very luminous red covering approximately 90 to 100% of the fruit skin surface, on a washed orange red background.

The pollen parent of the new variety, which is the 'SELECTION INRA 6062RT' apple variety (non patented), considering the observations we have made on our production site, ripens approximately during the second half of September, usually from September $13^{th}$, until September $26^{th}$. The REGALNAT variety ripens approximately at the same time in comparison with its pollen parent. 'REGALNAT' fruits are considered to be round and very regular whereas the shape of 'SELECTION INRA 6062RT' fruits is considered to be round and flattened. The skin color of 'SELECTION INRA 6062RT' fruits is considered red on approximately 80% of the fruit skin, whereas the fruit skin for 'REGALNAT' is colored with a very luminous red covering approximately 90 to 100% of the fruit skin surface, on a washed orange red background. The fruits of the 'SELECTION INRA 6062RT' have a fruit stem considered long, whereas the length of the fruit stem for the 'REGALNAT' variety fruits is considered medium to long.

The 'REGALYOU' (U.S. Plant Pat. No. 25,827) apple tree variety is considered as good pollinators for the new variety 'REGALNAT'.

DETAILED DESCRIPTION

Referring more specifically to the pomological details of this new and distinct variety of apple tree, the following has been observed on trees in their fourth growing season (third year of production) under the ecological conditions prevailing at the orchards located near the town of Elne, Pyrénées-Orientales department, France.

All observations have been done on rootstock cultivar. The rootstock was a 'M9EMLA' (non-patented) tree. All major color code designations are by reference to The R.H.S. Color Chart (Fourth Edition) provided by The Royal Horticultural Society of Great Britain.

Tree:

Generally: The first year the apple tree is generally cut at 2.50 meters height. The length in one year for each lateral shoot varies from 0.60 meters to 0.80 meters. We are cutting the apple trees during the second year to a height of 2.50 meters. The form of the apple trees is cylindrical and the diameter is limited to 1 meter.

*Size*.—Medium to high as compared to other commercial apple cultivars. The tree size the first year was approximately 2.50 meters. The tree was pruned during each following dormant season to a height of approximately 2.50 meters. Current season's shoots growth could reach 0.80 meters. So, the tree size from the second year (second and next years) reached a final height of 3.10 to 3.30 meters with current seasons shoots length comprised.

*Spread*.—Approximately 1.0 meter with a cylindrical shape. The whole orchard was oriented to a central leader organization, with tree lines spaced of 4.0 meters and trees spaced of 1 meter in a same tree line.

*Vigor*.—Medium to strong, tree growth reaches 0.60 to 0.80 meters the first growing season.

*Productivity*.—Good to very good productivity, every year and without alternation. The new variety produces adequate fruit set annually on a regular basis. The number of the fruit set varies with the prevailing climatic conditions and cultivar practices employed during the bloom period and is therefore not distinctive of the present variety.

*Bearer*.—Very regular every year.

*Type of bearing*.—On spurs and long shoots.

*Type*.—Ramified.

*Habit*.—Spreading.

*Form*.—Naturally semi-spread.

*Hardiness*.—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017,1017 hours in 2017-2018, 844 hours in 2018-2019, 706 hours in 2019-2020 showed a good behavior of the tree in all cases. No injury with temperatures as low as −12° C. in winter. Good resistance to late frosts.

Trunk:

*Size*.—Medium. Approximately 62.0 to 68.0 millimeters ($4^{th}$ growing season) above 20.0 centimeters above the ground.

*Bark texture*.—Rough with lenticels.

*Lenticels*.—Small number of lenticels. The number of lenticels reaches 2 lenticels per $cm^2$.

*Lenticels size*.—Approximately 1.0 millimeter height and between 2.0 and 3.0 millimeters width ($4^{th}$ growing season).

*Lenticels color*.—Color of lenticels is considered beige (RHS Greyed Orange 164 C or RHS Greyed Orange 164 D).

*Bark color*.—Brown to grey (RHS Grey 201 B or RHS Grey 201 C).

Branches:

*Diameter*.—Branches at the 2nd growing season have an average diameter of 7.0 to 11.0 millimeters.

*Surface texture*.—Rough.

*Lenticels*.—Lenticels on mature branches are medium with a diameter of about 1.0 to 2.0 millimeters and a stretched round shape. The number of lenticels reaches on mature branches 4 lenticels per $cm^2$. The lenticel color is beige (RHS Greyed Orange 165 C or RHS Greyed Orange 165 D).

*Color*.—Branches are brown (RHS Grey Brown N200 B).

*Crotch angles*.—Approximately 45.0 degrees from the supporting branch. This particular characteristic is not considered distinctive of the variety, however.

*Internode*.—Generally from 16.0 to 20.0 millimeters length.

Current season shoots:

*Diameter*.—Average diameter from 4.0 to 5.0 millimeters.

*Surface texture*.—Rough, with approximately 4 lenticels per $cm^2$.

*Lenticels*.—Considered medium with a diameter of 1.0 millimeter and a round shape. The lenticel color is beige (RHS Greyed Orange 165 C or RHS Greyed Orange 165 D).

*Crotch angles*.—Approximately 30 degrees from the supporting branch. This particular characteristic is not considered distinctive of the variety, however.

*Internode*.—Generally, from 18.0 millimeters to 21.0 millimeters length.

*Color*.—The color of current season shoots is considered brown (RHS Brown 200 B or RHS Brown 200 C) on lower part of shoots, and the color of the upper part is similar and colored in brown (RHS Brown 200 B or RHS Brown 200 C).

*Growth pattern of one year old shoots*.—Straight.

Bud scales:

*Size*.—Medium to large.

*Shape*.—Elongated and conic in shape.

*Surface texture*.—Pubescent.

*Color*.—The inside of the bud scales is yellow green (RHS Yellow Green 145 A) and the outside of the bud scales is purple brown (RHS Greyed Purple 183 A).

Leaves:

*Size*.—Medium for the species. The ratio leaf length/leaf width is 1.865.

*Length*.—The medium length is 91.0 millimeters without leaf petiole.

*Width*.—The medium width is 48.8 millimeters.

*Leaf form in transverse section*.—Concave.

*Leaf form*.—Entire.

*Apex*.—Acute.

*Base*.—Round-shaped.

*Margins*.—Slightly undulating.

*Margins shape*.—Crenate.

*Surface texture*.—A thin pubescence on lower surface of the leaves. No pubescence on upper surface.

*Thickness*.—Considered medium thick.

*Attitude of the leaf blade in relation to the shoot*.—Upwards.

Leaf color:

*Upper leaf surface*.—Green (RHS Green 147 A).

*Lower surface*.—A lighter green (RHS Yellow Green 148 B) than the upper leaf surface color.

Leaf veins:

*Leaf venation*.—Pinnately veined.

Mid-vein:

*Width*.—Approximately 1.5 millimeters.

*Color*.—Light green (RHS Yellow Green 145 C) to purple (RHS Greyed Red 181 A) at the basis, evolves with maturity.

Secondary veins:

*Color*.—Light green (RHS Yellow Green 145 D).

Leaf petioles:

*Size*.—Medium.

*Length*.—About 27.0 to 35.0 millimeters. The ratio between the leaf length and the petiole length is approximately 3.

*Diameter*.—About 2.0 to 2.5 millimeters.

*Color*.—The upper surface is brown, slightly purple (RHS Brown 200 A or RHS Brown 200 B). Lower surface is purple (RHS Greyed Purple 185 A).

*Shape*.—Smooth.

Leaf stipules:

*Generally*.—No leaf stipules were observed.

Flowers:

Flower buds:

*Generally*.—At pre-floral stage of development, the floral buds are made up with 5 buds having a conic shape with a round tip. Their form is evolving until blooming, with variables dimensions. Just before blooming, floral buds are approximately 4.0 to 5.0 millimeters in width and approximately 4.0 to 5.0 millimeters long. Just after blooming, the flower shoots are approximately 9.0 to 11.0 millimeters long and 5.0 to 6.0 millimeters in width.

*Distribution of flower buds*.—The distribution of the flower buds is considered homogenous on the trees. Flower buds are found in groups of 3 to 5.

*Color*.—This characteristic is dependent upon the proximity to bloom. At pre-floral stage of development, the bottom of the flowers buds, or calyx formed by sepals, or flower receptacle, is of green color (RHS GREYED GREEN 194 B to C). The corolla formed by petals, is generally pink to purple (RHS Greyed Purple 186 B or RHS Greyed Purple 186 C).

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally, in the middle of April. The first bloom was observed from April 8$^{th}$ until Apr. 17, 2011.

*Blooming time*.—Considered medium in relative comparison to other commercial apple cultivars grown in the Pyrénées-Orienteles department, France. The date of bloom varies slightly with climatic conditions and cultural practices. Thus, the full bloom was observed from April 8$^{th}$ until Apr. 17, 2011, then from April 12$^{th}$ until Apr. 24, 2012, then from April, 23$^{th}$ until May 4, 2013, then from April, 13$^{th}$ until Apr. 22, 2014, then from April 14$^{th}$ until Apr. 22, 2015, then from April 14$^{th}$ until Apr. 22, 2016, then from April 8$^{th}$ until Apr. 15, 2017, then from April 20$^{th}$ until Apr. 30, 2018, then from April 26$^{th}$ until May 3, 2019 and then from April 22$^{nd}$ until May 5, 2020.

*Blooming period*.—Average 8 to 14 days. This characteristic varies slightly with the prevailing climatic conditions.

*Flower type*.—The variety is considered to have a showy type flower (rosette).

*Flower size*.—Considered medium to large. Average diameter of the corolla is between 22.0 and 28.0 millimeters when totally opened.

*Flower bud frequency*.—Generally 5 to 6 flower buds appear per node.

*Fragrance*.—Sweet.

*Flower shape*.—Shallow cup.

Petal:

*Size*.—Considered medium for the species.

*Length*.—Generally between 12.0 and 12.5 millimeters.

*Width*.—Generally between 7.8 and 8.2 millimeters.

*Petal form*.—Round.

*Petal margins*.—Slightly undulating.

*Petal count*.—Usually 5.

*Arrangement of petals*.—Intermediate.

*Petal texture*.—Smooth.

*Petal color*.—White (RHS White 155 D) to pale pink.

*Fragrance*.—Soft.

Petal apex:

*Generally*.—The petal apices are generally round in shape.

Petal claw:

*Form*.—The claw is considered to have a narrow form.

*Length*.—Approximately 1.5 to 2.0 millimeters.

*Width*.—Approximately 1.5 millimeters.

*Color*.—White (RHS WHITE 155 D), similar to the petal color.

Flower pedicel:

*Length*.—Average length between 20.0 to 25.0 millimeters.

*Diameter*.—Between 1.7 and 1.8 millimeters.

*Color*.—Green (RHS Yellow Green 146 C or RHS Yellow Green 146 D).

Calyx:

*Color*. At the stage F of blooming, when the flower is open, the inner surface of the calyx, or flower receptacle, is of greenish color (RHS Yellow Green 153 D). The outer surface of the calyx is also considered green (RHS Green 138 A).

*Texture*.—The inner surface is smooth.

Sepals:
*Size*.—Usually considered medium.
*Length*.—Approximately 4.0 to 5.0 millimeters.
*Width*.—Approximately 3.0 to 4.0 millimeters.
*Number*.—Generally 5 sepals per flower.
*Sepal form*.—Triangular.
*Margins*.—Smooth.
*Texture*.—The sepal texture is smooth.
*Color*.—Upper surface of the sepals is green (RHS Greyed Green 194 B or RHS Greyed Green 194 C), and the lower surface is also green (RHS Greyed Green 194 C).

Stamens:
*Average number of stamens per flower*.—Approximately 12 to 15 stamens per flower.
*Size*.—Variable in length, approximately between 5.0 and 6.0 millimeters in length, generally higher than pistil's length.
*Size compared to petals*.—The size of stamens is smaller than the size of petals.
*Color*.—Considered white (RHS White 155 C).

Pistil:
*Generally*.—The pistil is composed with carpels. The pistil is considered smaller than the stamens.
*Length*.—Approximately 4.0 to 5.0 millimeters long including the ovary, smaller than stamen's length.
*Color*.—Considered light green (RHS Yellow Green 151 B to RHS Yellow Green 151 C).

Stigma:
*Diameter*.—Approximately 0.9 millimeter.
*Shape*.—Elliptic.
*Color*.—Light green (RHS Yellow Green 151 A).

Ovary:
*Length*.—Approximately 2.0 millimeters.
*Diameter*.—Approximately 2.0 millimeters.
*Texture*.—Pubescent.
*Color*.—Green (RHS Yellow Green 151 A).

Anthers:
*Size*.—Small.
*Form*.—Cordate.
*Color*.—Considered Green to slightly Yellow (RHS Yellow Green 154 C).

Pollen:
*Generally*.—Pollen is abundant and stamens are fertile.
*Color*.—Pollen has a yellow color (RHS Yellow 5 C) which may evolve with maturity.

Fruits:
*Maturity when described*.—Firm at maturity.
*Date of first picking*.—Sep. 10, 2011, varies slightly with climatic conditions.
*Date of last picking*.—Oct. 5, 2016 varies slightly with climatic conditions. The harvest is generally performed in two runs.
*Ripening period*.—The ripening period is considered late and begins during September. More particularly, the ripening period usually begins at the end of September. However, the ripening period sometimes begins earlier, namely at the beginning of September. Thus, last known picking times carry on from September 20$^{th}$ to Sep. 26, 2009, then from September 10$^{th}$ to Sep. 17, 2011, then from September 15$^{th}$ to Sep. 22, 2012, then from September 28$^{th}$ to Oct. 4, 2013, then from September 20$^{th}$ to Sep. 26, 2014, then from September 27$^{th}$ to Oct. 2, 2015, then from September 28$^{th}$ to Oct. 5, 2016, then from September 6$^{th}$ to Sep. 12, 2017, then from September 22$^{nd}$ to Sep. 29, 2018, and then from September 25$^{th}$ to Oct. 1, 2019.

Size:
*Generally*.—Considered large with a homogeneous size between the fruits.
*Average transversal diameter*.—About 74.0 to 81.0 millimeters.
*Average axial diameter*.—About 62.0 to 69.0 millimeters.
*Typical weight*.—Generally 204.0 grams. This characteristic is highly dependent upon the prevailing cultural practices, and therefore is not particularly distinctive of the variety.
*Position of the maximum diameter*.—At the middle of the fruit.

Fruit form:
*Generally*.—Round.
*Fruit ribbing*.—Absent.
*Fruit suture*.—Absent.
*Form of the ventral surface*.—Smooth.

Fruit stem:
*Generally*.—Considered medium to long.
*Length*.—Between 31.0 and 36.0 millimeters.
*Diameter*.—About 2.0 to 3.0 millimeters.
*Color*.—Light Brown (RHS Brown N199C).

Stem cavity:
*Form*.—Shallow.
*Depth*.—Medium, average depth between 9.0 and 11.0 millimeters.
*Width*.—Between 12.0 and 13.0 millimeters.

Fruit eye basin:
*Form*.—Round.
*Depth*.—Average depth between 8.0 and 10.0 millimeters.
*Width*.—Between 10.0 and 12.0 millimeters.

Calyx:
*Generally*.—Symmetrical, weakly opened.
*Form*.—Closed.
*Pubescence*.—The calyx shows a thin pubescence.

Fruit skin:
*Thickness*.—Considered medium and strong.
*Texture*.—Smooth and glabrous.
*Tendency to crack*.—None.

Lenticels:
*Number*.—High. About 5 lenticels per cm$^2$ of fruit skin.
*Size*.—Small.
*Form*.—Round.
*Diameter*.—Approximately 1.0 millimeter.
*Color*.—Light beige (RHS Greyed Orange 164 D).

Skin color:
*Over color*.—This over color is considered a luminous dark red (RHS Greyed Purple 185 A) and covers 90 to 100% of fruit skin, usually 98% of the fruit skin surface, on a washed orange red background.
*Pattern of over color*.—Only solid flush.
*Ground color*.—The ground color is a washed orange red (RHS Red 45 A) and covers at the most 10% of the fruit skin.
*Extent of anthocyanin overcolor of young fruit*.—Absent or very small.

Russeting:
*Russet around stem cavity*.—Very low.
*Russet on cheek*.—Absent or very weak.
*Russet around eye basin*.—Absent or very weak.

Flesh:

*Generally*.—Long shelf life after harvesting.

*Texture*.—Dense, crunchy, melty.

*Fibers*.—No fibers.

*Firmness*.—Firm.

*Aroma*.—Present.

*Juice*.—Juicy at ripeness.

*Taste*.—Balanced between acidity and sweetness, good and aromatic.

*Brix*.—Superior to 13.8 degrees until 14.7 degrees. The medium Brix is 14.3 degrees and varies slightly with amount of fruit per tree and climatic conditions.

*Acidity*.—Medium.

*Color*.—Cream (RHS Yellow White 158 A) at ripening time.

*Aperture of locules in transverse section*.—Closed.

*Width of locules*.—Approximately 3.0 millimeters.

*Length of locules*.—7.0 millimeters.

*Form of locules*.—Flattened.

*Vascular bundles*.—The number of vascular bundles is 10.

Fruit core:

*Form*.—Symmetrical.

*Position*.—At the middle of the fruit.

*Distinctness of core line*.—Distinct.

*Stamens*.—Visible.

Seeds:

*Count*.—Generally 10 seeds are present per fruit.

*Number of seeds per locule*.—Usually 2 seeds per locule.

*Size*.—Medium.

*Length*.—Approximately 9.0 millimeters.

*Width*.—Approximately 5.0 millimeters.

*Form*.—Ovoid.

*Texture*.—Smooth.

*Color*.—Considered Brown (RHS Brown 200 C) at ripeness.

Use: Dessert, fresh products, fruit juice.

*Market*.—Local and long distance. On the tree fruits can stay 10 days while keeping good gustative qualities. The lifetime after picking is also good.

Keeping quality: Good, held well for 3 to 4 months in cold storage at 1° C. and maintained good appearance and eating quality. At room temperature (18° C.), fruits are well preserved for about 2 months.

Shipping quality: Good, showed minimal bruising or scarring during picking, packing and shipping trials.

Plant/fruit disease resistance/susceptibility: In our growing conditions, no particular symptom was noticed. The 'REGALNAT' apple tree seems to be not much sensitive to russeting or bitter pit, to apple withering, to rot, to *Monilia* or *Oidium*, to aphids, to leafhopper. The new variety also seems to resistant to apple scab.

Robustness to winter: Very good for trees and flower buds.

Tolerance to dryness: Good.

The present new variety of apple tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of apple tree, substantially as illustrated and described, essentially characterized by its large size, and also characterized by its high yield and its round slightly flattened shape, its luminous dark red skin color, its firmness, and exceptional eating quality; the fruit is further characterized by its good handling, its tolerance to main apple pests and diseases and its storage qualities.

* * * * *